United States Patent [19]

Milano et al.

[11] Patent Number: 4,888,047
[45] Date of Patent: Dec. 19, 1989

[54] ACYLAMINOARYLOXY AND ARYLTHIO PYRIMIDINES AS HERBICIDES

[75] Inventors: Pamela D. Milano, Concord; Donald R. James, El Sobrante, both of Calif.

[73] Assignee: ICI Americas Inc., Wilmington, Del.

[21] Appl. No.: 176,510

[22] Filed: Apr. 1, 1988

Related U.S. Application Data

[63] Continuation of Ser. No. 789,279, Oct. 18, 1985, abandoned.

[51] Int. Cl.[4] .................... A01N 43/48; C07D 239/02
[52] U.S. Cl. ........................................ 71/92; 544/316
[58] Field of Search ........................... 544/316; 71/92

[56] References Cited

U.S. PATENT DOCUMENTS

| | | | |
|---|---|---|---|
| 3,126,271 | 3/1964 | Thomson et al. | 544/316 |
| 4,001,234 | 1/1977 | Johnston | 544/316 |
| 4,248,618 | 2/1981 | Serban et al. | 544/316 |
| 4,427,437 | 1/1984 | Serban et al. | 544/316 |
| 4,627,871 | 12/1986 | Sasse et al. | 544/316 |
| 4,659,362 | 4/1987 | Watson et al. | 544/316 |

FOREIGN PATENT DOCUMENTS 56-29576  3/1981  Japan ....................... 544/316

Primary Examiner—Mary C. Lee
Assistant Examiner—Robert C. Whittenbaugh
Attorney, Agent, or Firm—Denis A. Polyn

[57] ABSTRACT

As new compounds, acylaminoaryloxy and arylthio pyrimidines having the formula

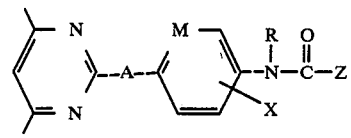

wherein A is oxygen or sulfur; M is CH or N; X is hydrogen, lower alkyl, halo, methoxy, alkoxy, $C_1$–$C_3$ alkylthio, cyano, carbomethoxy or trifluoromethyl;

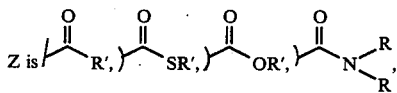

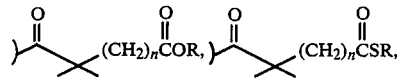

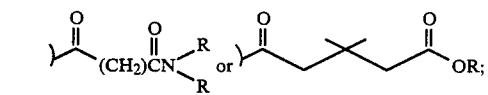

wherein R' is $C_1$–$C_8$ straight, branched-chain or haloalkyl, aryl; and R is hydrogen, $C_1$–$C_8$ straight or branched chain alkyl, $C_5$ or $C_6$ cycloalkyl or aryl.

3 Claims, No Drawings

ACYLAMINOARYLOXY AND ARYLTHIO PYRIMIDINES AS HERBICIDES

This application is a continuation of Ser. No. 06/789,279 filed Oct. 18, 1985, now abandoned.

BACKGROUND OF THE INVENTION

The present invention relates to certain acylaminoaryloxy pyrimidines and acylaminoarylthio pyrimidines which are particularly useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

The prior art contains numerous examples of pyrimidine-based compounds which have been disclosed to be herbicidally effective against a variety of weed pests. Examples of such prior art references include U.S. Pat. Nos. 4,001,234 and 4,427,437.

Still other patents, i.e., European patent application Publication No. 0,001,187, discloses 2-phenoxy and 2-phenylthio pyrimidine compounds useful as pre-emergent and post-emergent herbicides. In addition, U.S. Pat. No. 3,126,271, Tomson et al., also relates to certain pyrimidine compounds and to a method of controlling weeds with the use of these compounds.

Efforts are constantly being made, however, to find compounds which are equal to or greater in effectiveness than presently existing compounds, or which are more economical to produce.

DESCRIPTION OF THE INVENTION

It has now been discovered that certain new and novel acylamino aryloxy and acylaminoarylthio pyrimidines have good herbicidal and plant growth regulating activity, particularly when applied as post-emergent herbicides and used against annual and perennial grasses, and broadleaf weed pests.

As used herein, the term "herbicide" means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing and the like.

The new and novel compounds of this invention are acylaminoaryloxy pyrimidines and acylaminoarylthio pyrimidines.

These compounds have the formula

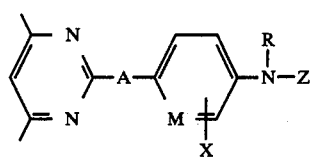

wherein
A is oxygen or sulfur;
M is CH or N;
X is hydrogen, lower alkyl, halo, methoxy, alkoxy, $C_1$–$C_3$ alkylthio, cyano, carbomethoxy or trifluoromethyl;

Z is

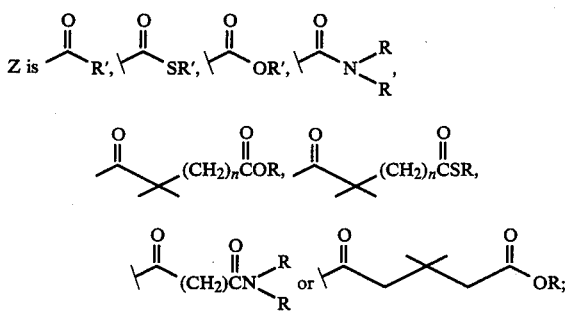

wherein
R' is $C_1$–$C_8$ straight, branched-chain or halo-alkyl, aryl; and
R is hydrogen, $C_1$–$C_8$ straight or branched chain alkyl, $C_5$ or $C_6$ cycloalkyl or aryl.

These compounds have been found to have especially good herbicidal activity against broadleaf weed pests when applied as a post-emergent herbicide. They are also effective as pre-emergent herbicides and plant growth regulators, but not to the same extent as when applied post-emergent.

Preferred compounds include:
2,2-dimethyl-N-[4-[(4,6-dimethylpyrimidin-2-yl)thio]phenyl]pentanamide;
2-chloro-N-[4-[(4,6-dimethylpyrimidin-2-yl)thio]phenyl]butanamide;
2,2-dimethyl-N-[4-[(4,6-dimethylpyrimidin-2-yl)thio]-2-methylphenyl] propanamide;
2,2-dimethyl-N-[4-[(4,6-dimethylpyrimidin-2-yl)thio]phenyl] propanamide;
2,2-dimethyl-N-[4-[(4,6-dimethylpyrimidin-2-yl)thio]-3-fluorophenyl] propanamide;
N-[3-chloro-[4-(4,6-dimethylpyrimidin-2-yl)thio]phenyl]-2,2-dimet hylpropanamide;
3-chloro-N-[4-[(4,6-dimethylpyrimidin-2-yl)thio]phenyl]-2,2-dimet hylpropanamide;
N-[4-[(4,6-dimethylpyrimidin-2-yl)thio]phenyl]-2-methylpropanamide;
N-[4-[(4,6-dimethylpyrimidin-2-yl)thio]phenyl]-2-methylbutanamide; and
2,2-dimethyl-N-[4-[(4,6-dimethylpyrimidin-2-yl)oxy]phenyl]propanamide.

The compounds 2-chloro-N-[4-[(4,6-dimethylpyrimidin-2-yl)thio]-phenyl]butanamide and 2,2-dimethyl-N-[4-[4(4,6-dimethylpyrimidin-2-yl)-thio]phenyl]pentanamide have rice selectivity. They control boardleaf and grassy weeds growing in and amongst the rice plants in a post-emergent application.

The preparation of the compounds of this invention is described below.

1. Oxygen Analogs 4,6-Dimethyl-2-chloropyrimidine is prepared according to the procedure of Marshall and Walker, *J. Chem. Soc.,* 1004 (1951). The corresponding pyrimidinyloxyaniline is prepared by simple displacement of the reactive 2-halogen by treatment with 4-aminophenol and potassium carbonate.

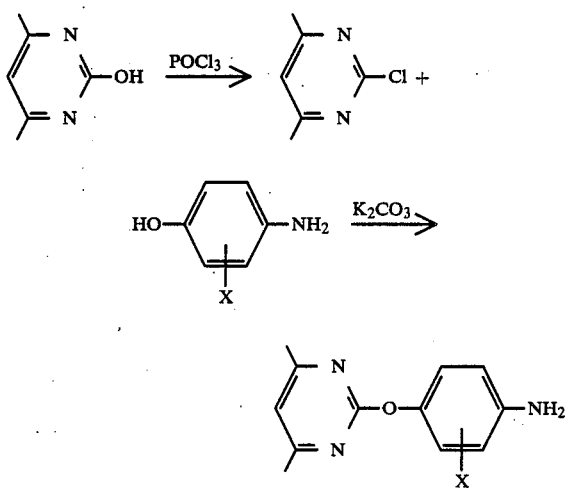

The acylation of the aniline is carried out by treatment with an acid chloride, chloroformate, chlorothioformate or dialkylcarbamyl chloride and a catalytic amount of 4-dimethyl-aminopyridine (DMAP) in pyridine.

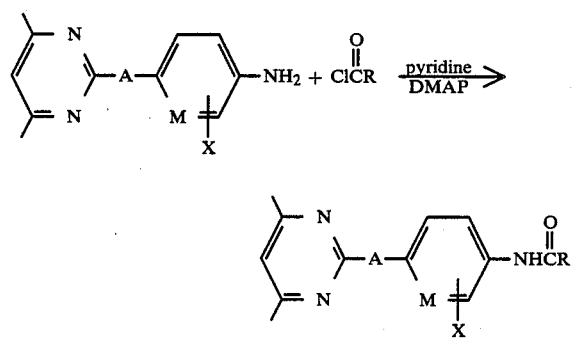

wherein
R=R'=alkyl, branched alkyl, aryl, etc;
R=OR';
R=SR'; and
R=N(R')$_2$

The synthesis of mercaptopyrimidines has been reviewed in "The Chemistry of Heterocyclic Compounds", a series published by Interscience Publ., New York and London, "The Pyrimidines", Vol. XVI of the series. Accordingly, 4,6-dimethyl-2-mercaptopyrimidine is prepared by condensing thiourea and 1,3-pentanedione in ethanolic hydrochloric acid.

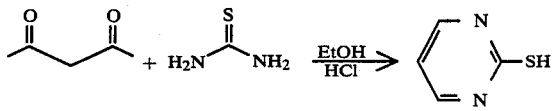

Pyrimidinylthioanilines were prepared by displacement of halogen from an aromatic or heteroaromatic nitro compound with the mercaptopyridine and potassium carbonate. Nitro compounds thus obtained are reduced to anilines by a standard procedure using iron and a catalytic amount of hydrochloric acid in aqueous ethanol.

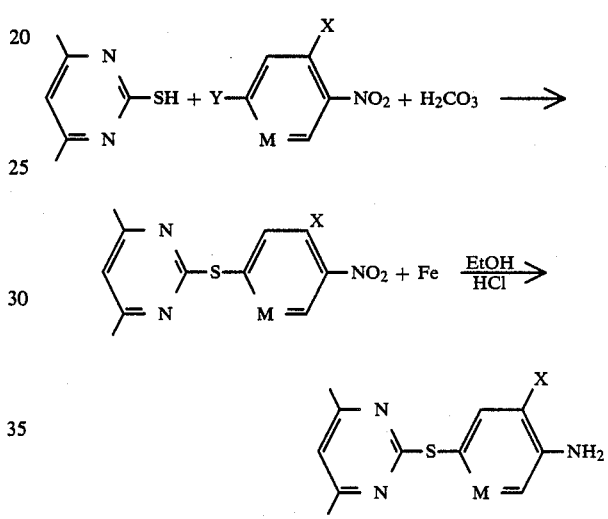

wherein Y=F, Cl; and M—CH, N.

Acylation of pyrimidinylthioanilines are carried out as presented above in the case of oxygen analogs.

N,N-disubstituted amides are prepared by treatment of an N-arylamide with an alkyl halide in a two-phase mixture of benzene and 50% sodium hydroxide using a catalytic amount of tetrabutylphosphonium bromide (TBPB).

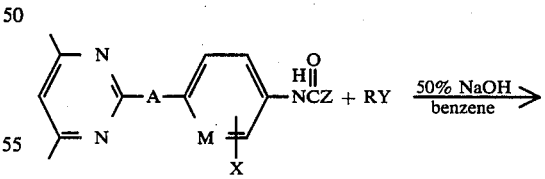

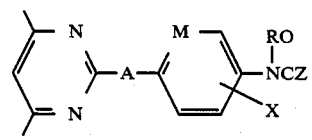

where Y=Cl, Br or I.

Ureas can be synthesized by treatment of an aniline with an isocyanate in dry methylene chloride using a catalytic amount of diazobicyclooctane (DABCO).

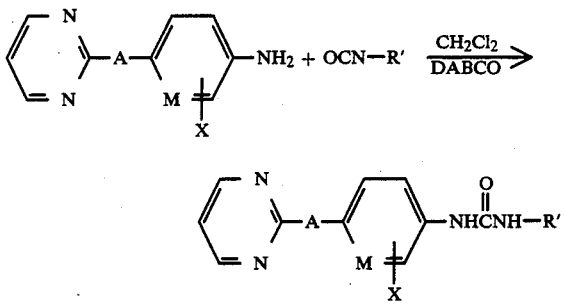

EXAMPLE 1

4,6-dimethyl-2-(4-nitrophenyl)pyrimidine

A solution of 25.0 grams (g) 4,6-dimethyl-2-mercaptopyrimidine, 25.1 g 4-fluoronitrobenzene and 24.6 g potassium carbonate in 750 milliliters (ml) acetonitrile was refluxed for 16 hours. The solution was then filtered hot through a pad of dicalite. The dicalite was washed with 300 ml hot acetonitrile. The solvent was evaporated from the combined filtrates giving a waxy yellow solid. This solid was triturated with hexanes giving 42.5 g yellow solid.

EXAMPLE 2

4-[(4,6-dimethylpyrimidin-2-yl)thio]aniline

A 250 ml 3-necked flask was equipped with mechanical stirrer, condensor and thermometer. To this was added in the following order: 4.6 g iron powder, 50 ml water, 60 ml ethanol and 0.5 ml concentrated hydrochloric acid. The mixture was heated to reflux with a heating mantle. The heating mantle was then removed and when the reflux subsided (temp about 76° C.) a small portion of 4,6-dimethyl-2-[(4-nitrophenyl)thio]pyrimidine was then carefully added. The rest of the 4,6-dimethyl-2-[(4-nitrophenyl)thio]pyrimidine, a total of 7.1 g was added over a period of about one hour and the solution was refluxed for 5 minutes. The heating mantle was removed and the temperature allowed to drop to 68° C. 0.5 g ($4.08 \times 10^{-3}$ moles) 50% sodium hydroxide was added to the solution and vigorous stirring was continued for 5 minutes. The solution was heated to 75° and filtered through a pad of dicalite. The dicalite was washed with 200 ml hot ethanol. The combined filtrates were stripped giving a tan solid. The solid was triturated with water and dried in a vacuum drying oven. A light tan solid (5.9g) was obtained.

EXAMPLE 3

N-[4-[(4,6-Dimethylpyrimidine-2-yl)thio]phenyl]benzamide

A solution of 1.5 g 4-[(4,6-dimethylpyrimidin-2-yl)thio]aniline, 0.9 g benzoyl chloride and about 0.1 g of 4-dimethylaminopyridine (DMAP) in 25 ml pyridine was stirred for 16 hours at room temperature. The solvent was evaporated and the resulting yellow solid was partitioned between 250 ml ethyl acetate and 150 ml water. The ethyl acetate solution was then washed with $2 \times 150$ ml water and dried over $Na_2SO_4$. The solvent was evaporated giving 2.0 g off-white solid, m.p. 190°–192° C. The structure was confirmed by infrared, nuclear magnetic resonance and mass spectral analysis as that of the desired product, N-[4-[(4,6-dimethylpyrimidin-2-yl)thio]phenyl]benzamide.

EXAMPLE 4

N-[4-[(4,6-Dimethylpyrimidin-2-yl)thio]phenyl]-N'-phenylurea

A solution of 1.5 g 4-[(4,6-dimethylpyrimidin-2-yl)thio]aniline, 0.8 g phenyl isocyanate an about 0.1 g diazobicyclooctane in 100 ml dry methylene chloride (passed through a column of neutral alumina) was stirred for 16 hours at room temperature. The solvent was then evaporated, giving 2.2 g off-white solid, m.p. 196°–200° C. The structure was confirmed by infrared, nuclear magnetic resonance and mass spectral analysis as that of the desired product, N-[4-[(4,6-dimethylpyrimidin-2-yl)thio]phenyl]-N'-phenylurea.

EXAMPLE 5

N-[4-[-(4,6-dimethylpyrimidin-2-yl)thio]phenyl]-N-methylhexanamide

Four grams N-[4-[(4,6-dimethylpyrimidin-2-yl)thio]phenyl]hexanamide, 3.4 g methyl iodide and 0.4 g tetrabutylphosphonium bromide was dissolved in a mixture of 10 ml 50% NaOH and 50 ml benzene. This was stirred vigorously at room temperature for 72 hours. Fifty milliliters water was then added and the benzene layer was separated off. The benzene solution was washed with $4 \times 100$ ml water then dried over $Na_2SO_4$. The solvent was evaporated giving 3.5 g dark brown oil. The oil was chromatographed on silica gel eluted with 50% ethyl acetate/hexanes giving 2.5 g yellow oil which slowly crystallized. Melting point of the resulting pale yellow wolid was 61°–63° C. The structure was confirmed by infrared, nuclear magnetic resonance and mass spectral analysis as that of the desired product, N-[4[(4,6-dimethylpyrimidin-2-yl)thio]phenyl]-N-methylhexanamide.

TABLE I

| Cmpd. No. | A | M | X | Z | R |
|---|---|---|---|---|---|
| 1 | S | CH | H | )—C(=O)—phenyl | H |
| 2 | S | CH | H | )—C(=O)—(butyl chain) | H |
| 3 | S | CH | H | )—C(=O)—(propyl) | H |
| 4 | S | CH | H | )—CO—(ethyl) | H |
| 5 | S | CH | H | )—C(=O)—(isopropyl) | H |

TABLE I-continued

Structure: pyrimidine(4,6-dimethyl)—A—(pyridine with M, X)—N(R)—Z

| Cmpd. No. | A | M | X | Z | R |
|---|---|---|---|---|---|
| 6 | S | CH | H | —C(=O)—(CH$_2$)$_5$CH$_3$ | H |
| 7 | S | CH |  | —C(=O)—(CH$_2$)$_4$CH$_3$ | CH$_3$ |
| 8 | S | CH | H | —C(=O)—(3-Cl-phenyl) | H |
| 9 | S | CH | H | —C(=S)—CH$_2$CH$_3$ | H |
| 10 | S | CH | H | —C(=O)—CH(CH$_2$CH$_3$)(CH$_2$CH$_2$CH$_3$) | H |
| 11 | S | CH | H | —C(=O)—cyclohexyl | H |
| 12 | S | CH | H | —C(=O)—CH$_2$CH$_3$ | H |
| 13 | S | CH | H | —C(=O)—O—CH$_2$CH$_2$CH$_3$ | H |
| 14 | S | CH | H | —C(=O)—CH=C(CH$_3$)$_2$ | H |
| 15 | S | CH | H | —C(=O)—CHCl$_2$ | H |
| 16 | S | CH | H | —C(=O)—O—CH(CH$_3$)$_2$ | H |
| 17 | S | CH | H | —C(=O)—C(CH$_3$)$_3$ | H |
| 18 | S | CH | H | —C(=S)—C(CH$_3$)$_3$ | H |
| 19 | S | CH | H | —C(=O)—CH$_2$CH(CH$_3$)$_2$ | H |
| 20 | S | CH | H | —C(=O)—CH(CH$_2$CH$_3$)$_2$ | H |
| 21 | S | CH | H | —C(=O)—C(CH$_3$)$_3$ | H |
| 22 | S | CH | H | —C(=O)—CH$_2$CH$_2$CH$_3$ | H |
| 23 | S | CH | H | —C(=O)—CHCl—CH$_3$ | H |
| 24 | S | CH | 3-Cl | —C(=O)—CH(CH$_3$)$_2$ | H |
| 25 | S | CH | H | —C(=O)—C(CH$_3$)$_2$CH$_2$CH$_3$ | H |
| 26 | S | CH | H | —C(=O)—CH(CH$_3$)CH$_2$CH$_3$ | H |
| 27 | O | CH | H | —C(=O)—C(CH$_3$)$_3$ | H |
| 28 | S | CH | H | —C(=O)—CHCl—CH$_2$CH$_3$ | H |
| 29 | S | CH | H | —C(=O)—cyclopropyl | H |
| 30 | S | CH | 3-Cl | —C(=O)—C(CH$_3$)$_3$ | H |
| 31 | S | CH | 2-CH$_3$ | —C(=O)—C(CH$_3$)$_3$ | H |
| 32 | S | CH | H | —C(=O)—C(CH$_3$)$_2$CH$_2$Cl | H |
| 33 | S | CH | H | —C(=O)—C(CH$_3$)(cyclopropyl) | H |

TABLE I-continued

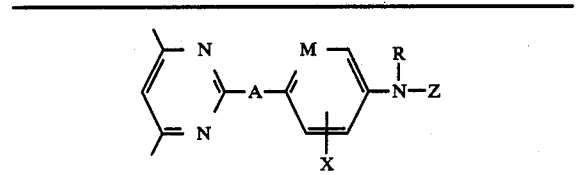

| Cmpd. No. | A | M | X | Z | R |
|---|---|---|---|---|---|
| 34 | S | CH | H | -C(=S)-CH(CH3)CH2CH3 (thio ester, sec-butyl) | H |
| 35 | S | CH | 3-CH3 | -C(=O)-C(CH3)3 | H |
| 36 | S | CH3 | H | -C(=O)-(3,5-dichlorophenyl) | H |
| 37 | S | CH | 3-F | -C(=O)-C(CH3)3 | H |
| 38 | S | CH | H | -C(=O)-S-CH2CHClCH2Cl | H |
| 39 | S | CH | H | -C(=O)-CH2CH2CH3 | H |
| 40 | S | CH | H | -C(=O)-CH2CH2CH2CH3 | H |
| 41 | S | CH | H | -C(=O)-CH2CH(CH3)2 | H |
| 42 | S | CH | H | -C(=S)-CH2CH(CH3)CH3 | H |
| 43 | S | N | H | -C(=O)-C(CH3)3 | H |
| 44 | S | N | H | -C(=O)-C(CH3)2CH2CH3 | H |
| 45 | S | CH | H | -C(=O)-phenyl | H |
| 46 | S | CH | H | -O-C(=O)-O-C(CH3)(CCl3) | H |
| 47 | S | CH | H | -C(=O)-N(CH3)2 | H |

TABLE I-continued

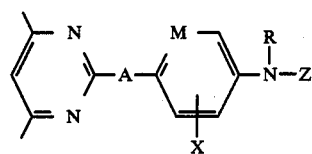

| Cmpd. No. | A | M | X | Z | R |
|---|---|---|---|---|---|
| 48 | S | CH | H | -C(=O)-NH-phenyl | H |
| 49 | S | CH | H | -C(=O)-NH-(3-CF3-phenyl) | H |
| 50 | S | CH | H | -C(=O)-NH-(3-Cl-phenyl) | H |
| 51 | S | CH | H | -C(=O)-N(CH3)(OCH3) | H |
| 52 | S | CH | H | -C(=O)-CH(CH3)2 | CH3 |
| 53 | S | CH | H | -C(=O)-C(Cl)2-cyclopropyl (CCl2 ring) | H |
| 54 | S | CH | 3-Cl | -C(=O)-CH(CH3)CH2CH3 | H |
| 55 | S | CH | 2-CH3 | -C(=O)-C(CH3)2CH2CH3 | H |
| 56 | S | CH | 2-CH3 | -C(=O)-CH(CH3)CH2CH3 | H |
| 57 | S | CH | N | -C(=O)-CH2-C(CH3)2-C(=O)-O-CH(CH3)2 | H |
| 58 | S | CH | 3-CF3 | -C(=O)-C(CH3)3 | H |
| 59 | S | CH | 2-CF3 | -C(=O)-C(CH3)3 | H |
| 60 | S | CH | 2-OCH3 | -C(=O)-C(CH3)3 | H |
| 61 | S | CH | 2-OCH3 | -C(=O)-C(CH3)3 | H |

TABLE I-continued

[Structure: pyrimidine-A-phenyl(X)-N(R)-Z core]

| Cmpd. No. | A | M | X | Z | R |
|---|---|---|---|---|---|
| 62 | S | CH | H | —C(=O)—CH(Br)—CH(CH₃)₂ | H |
| 63 | S | CH | H | —C(=O)—CH(Br)—CH₂CH₃ | H |
| 64 | S | CH | H | —C(=O)—CH(CH₃)₂ | H |
| 65 | S | CH | H | —C(=O)—CH(—C(=O)—O—CH(CH₃)₂)— | H |
| 66 | S | CH | H | —C(=O)—CH₂—CH(—C(=O)—O—CH(CH₃)₂)— | H |

The herbicidal activity of the preferred compound of the invention as exhibited by means of tests in accordance with the following procedure.

EXAMPLE 2

Herbicidal Activity Tests

This example offers herbicidal activity test data to show the effectiveness of the amide compounds of the invention. The effect is observed by comparing the extent of weed control in test flats treated with the compounds against that occurring in similar control flats. The soil used in these tests was a sandy loam soil from the Livermore, California area.

Also added to the soil was 17-17-17 fertilizer (N-$P_2O_5$-$K_2O$ on a weight basis), amounting to 100 ppm by weight with respect to the soil and 200 ppm Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABR |
|---|---|---|
| GRASSES: | | |
| annual ryegrass | *Lolium multiflorum* | ARG |
| watergrass | *Echinochloa crusgalli* | WG |
| shattercane | *Sorghum bicolor* | SHC |
| wild oat | *Avena fatua* | WO |
| broadleaf signalgrass | *Brachiaria platyphylla* | BSG |
| green foxtail | *Setaria viridis* | FT |
| yellow nutsedge | *Cyperus esculentus* | YNS |
| Broadleaf Weeds | | |
| sicklepod | *Cassia obtusifolia* | SP |
| sesbania | *Sesbanis exaltata* | SESB |
| cocklebur | *Xanthium pensylvanicum* | CB |
| annual morningglory | *Ipomea purpurea* | AMG |
| velvetleaf | *Abuliton theoprasti* | VL |
| mustard | *Brassica juncea* | MD |
| curly dock | *Rumex crispus* | CD |

Crop plants were also planted at the same time. These were as follows:

| CROP PLANTS | | |
|---|---|---|
| sugarbeets | *Beta vulgaris* | SB |
| soybeans | *Glycine max* | SOY |
| rice | *Oryzae sativa* | RC |
| cotton | *Gossypium hirsutum* | COT |
| corn | *Zea mays* | CN |
| wheat | *Triticum aestivum* | WH |
| milo | *Sorghum bicolor* | ML |

Sufficient seeds were planted to produce several seedlings per inch in each row. The flats were then placed in a greenhouse maintained at 70° to 85° F. (21° to 30° C.) and watered daily by sprinkler.

In pre-emergent testing (PES) the herbicide is incorporated into the soil prior to planting of the seeds.

In post-emergent testing (POST) chemical application is made by spraying 12 days after planting. The spray solution is prepared by dissolving 84 mg of herbicide compound in 20 ml of acetone containing 0.5% Tween® 20 (polyoxysorbitan monolaurate), then adding 20 ml of water to the resulting solution. The solution is sprayed at 25 gallon/acre. Other rates are achieved by varying the solution concentration and/or the rate of spray.

Approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in Tables I and II below.

TABLE I

HERBICIDE TEST RESULTS

| Compound Number | Application Rate (lb/A) | Method | FT | WG | WO | AMG | VL | MD | CD | YNS |
|---|---|---|---|---|---|---|---|---|---|---|
| 1 | 4.00 | PES | 0 | 0 | 0 | 0 | 0 | 0 | 0 | 0 |
|   | 4.00 | POST | 0 | 0 | 0 | 30 | 40 | 100 | 20 | 0 |
| 2 | 4.00 | PES | 0 | 0 | 0 | 0 | 0 | 0 | 0 | 0 |
|   | 4.00 | POST | 100 | 20 | 30 | 100 | 90 | 100 | 100 | 0 |
| 3 | 4.00 | PES | 0 | 0 | 0 | 0 | 30 | 70 | 0 | 0 |
|   | 4.00 | POST | 100 | 30 | 90 | 100 | 100 | 100 | 100 | 0 |
| 4 | 4.00 | PES | 0 | 0 | 0 | 0 | 100 | 100 | 60 | 0 |
|   | 4.00 | POST | 100 | 0 | 0 | 60 | 70 | 100 | 100 | 0 |
| 5 | 4.00 | PES | 70 | 20 | 55 | 100 | 100 | 100 | 70 | 0 |
|   | 4.00 | POST | 100 | 100 | 90 | 100 | 100 | 100 | 100 | 0 |
| 6 | 4.00 | PES | 20 | 15 | 25 | 0 | 0 | 40 | 20 | 0 |
|   | 4.00 | POST | 20 | 20 | 0 | 30 | 0 | 100 | 0 | 0 |
| 7 | 4.00 | PES | 0 | 0 | 0 | 0 | 0 | 100 | 0 | 0 |

TABLE I-continued
HERBICIDE TEST RESULTS

| Compound Number | Application Rate (lb/A) | Method | FT | WG | WO | AMG | VL | MD | CD | YNS |
|---|---|---|---|---|---|---|---|---|---|---|
| | 4.00 | POST | 0 | 15 | 0 | 50 | 80 | 100 | 0 | 0 |
| 8 | 4.00 | PES | 20 | 15 | 0 | 10 | 0 | 80 | 0 | 0 |
| | 4.00 | POST | 70 | 0 | 0 | 100 | 100 | 100 | 60 | 0 |
| 9 | 4.00 | PES | 0 | 0 | 0 | 0 | 0 | 0 | 0 | 0 |
| | 4.00 | POST | 75 | 40 | 0 | 100 | 80 | 100 | 100 | 0 |
| 10 | 4.00 | *PES | 0 | 0 | 0 | 0 | 0 | 0 | 0 | 0 |
| | 4.00 | POST | 80 | 20 | 0 | 40 | 30 | 100 | 70 | 0 |
| 11 | 4.00 | PES | 0 | 0 | 0 | 0 | 0 | 0 | 0 | 0 |
| | 4.00 | POST | 100 | 20 | 30 | 70 | 70 | 100 | 90 | 0 |
| 12 | 4.00 | PES | 0 | 0 | 0 | 0 | 0 | 0 | 0 | 0 |
| | 4.00 | POST | 100 | 30 | 40 | 100 | 100 | 95 | 90 | 0 |
| 13 | 4.00 | PES | 0 | 25 | 0 | 15 | 0 | 100 | 100 | 0 |
| | 4.00 | POST | 100 | 20 | 0 | 100 | 35 | 100 | 100 | 0 |
| 14 | 4.00 | PES | 0 | 0 | 0 | 0 | 0 | 0 | 0 | 0 |
| | 4.00 | POST | 15 | 0 | 0 | 15 | 100 | 100 | 0 | 0 |
| 15 | 4.00 | PES | 15 | 65 | 20 | 45 | 70 | 100 | 20 | 0 |
| | 4.00 | POST | 70 | 35 | 30 | 100 | 90 | 100 | 75 | 0 |
| 16 | 4.00 | PES | 100 | 100 | 90 | 98 | 100 | 100 | 100 | 10 |
| | 4.00 | POST | 100 | 100 | 100 | 100 | 100 | 100 | 100 | 35 |
| 17 | 4.00 | PES | 0 | 0 | 0 | 0 | 0 | 0 | 95 | N |
| | 4.00 | POST | 50 | 25 | 0 | 70 | 80 | 100 | 100 | 0 |
| 18 | 4.00 | PES | 80 | 80 | 0 | 85 | 95 | 100 | 95 | N |
| | 4.00 | POST | 100 | 100 | 100 | 100 | 100 | 100 | 100 | 0 |
| 19 | 4.00 | PES | 85 | 90 | 0 | 75 | 85 | 100 | 95 | N |
| | 4.00 | POST | 100 | 95 | 100 | 100 | 100 | 100 | 100 | 0 |
| 20 | 4.00 | PES | 40 | 15 | 0 | 0 | 40 | 90 | 90 | N |
| | 4.00 | POST | 90 | 40 | 10 | 100 | 95 | 100 | 100 | 0 |
| 21 | 4.00 | PES | 25 | 0 | 0 | 0 | 0 | 0 | 0 | 0 |
| | 4.00 | POST | 100 | 40 | 0 | 100 | 50 | 90 | 90 | 0 |
| 22 | 4.00 | PES | 0 | 0 | 0 | 0 | 0 | 0 | 0 | 0 |
| | 4.00 | POST | 90 | 25 | 0 | 95 | 95 | 95 | 90 | 0 |
| 23 | 4.00 | PES | 25 | 0 | 0 | 80 | 80 | 100 | 100 | N |
| | 4.00 | POST | 95 | 95 | 95 | 100 | 100 | 100 | 100 | 0 |
| 24 | 4.00 | PES | 100 | 100 | 25 | 95 | 90 | 100 | 100 | 0 |
| | 4.00 | POST | 100 | 100 | 100 | 100 | 100 | 100 | 100 | N |
| 25 | 4.00 | PES | 100 | 100 | 50 | 100 | 100 | 100 | 90 | 0 |
| | 4.00 | POST | 100 | 100 | 100 | 100 | 100 | 100 | 100 | N |
| 26 | 4.00 | PES | 100 | 100 | 50 | 100 | 100 | 100 | 90 | 0 |
| | 4.00 | POST | 100 | 100 | 100 | 100 | 100 | 100 | 100 | N |
| 27 | 4.00 | PES | 65 | 0 | 0 | 30 | 35 | 100 | 0 | 0 |
| | 4.00 | POST | 100 | 25 | 85 | 100 | 95 | 100 | 85 | 0 |
| 28 | 4.00 | PES | 65 | 70 | 0 | 75 | 15 | 100 | 85 | 0 |
| | 4.00 | POST | 50 | 25 | 0 | 85 | 35 | 95 | 75 | 0 |
| 29 | 4.00 | PES | 85 | 25 | 0 | 0 | 0 | 100 | 100 | 0 |
| | 4.00 | POST | 100 | 100 | 50 | 95 | 100 | 100 | 100 | 0 |
| 30 | 4.00 | PES | 85 | 25 | 0 | 0 | 0 | 100 | 100 | 0 |
| | 4.00 | POST | 100 | 100 | 50 | 95 | 100 | 100 | 100 | 0 |
| 31 | 4.00 | PES | 100 | 100 | 50 | 90 | 100 | 100 | 100 | 0 |
| | 4.00 | POST | 100 | 100 | 100 | 100 | 100 | 100 | 85 | 50 |
| 32 | 4.00 | PES | 100 | 100 | 0 | 85 | 100 | 100 | 100 | 0 |
| | 4.00 | POST | 100 | 100 | 95 | 100 | 100 | 100 | 95 | 0 |
| 34 | 4.00 | PES | 100 | 0 | 0 | 0 | 95 | 100 | 90 | 0 |
| | 4.00 | POST | 100 | 20 | 20 | 100 | 85 | 100 | 85 | 0 |
| 35 | 4.00 | PES | 95 | 90 | 0 | 60 | 100 | 100 | 90 | 0 |
| | 4.00 | POST | 95 | 25 | 0 | 100 | 100 | 100 | 90 | 0 |
| 37 | 4.00 | PES | 100 | 95 | 0 | 100 | 100 | 100 | 100 | 0 |
| | 4.00 | POST | 100 | 100 | 100 | 100 | 100 | 100 | 100 | 0 |
| 38 | 4.00 | PES | 0 | 0 | 0 | 0 | 0 | 0 | 0 | 0 |
| | 4.00 | POST | 50 | 35 | 10 | 35 | 35 | 100 | 100 | 0 |
| 39 | 4.00 | PES | 0 | 0 | 0 | 0 | 0 | 100 | 100 | 0 |
| | 4.00 | POST | 100 | 100 | 25 | 100 | 90 | 100 | 90 | 0 |
| 40 | 4.00 | PES | 0 | 0 | 0 | 0 | 0 | 25 | 0 | 0 |
| | 4.00 | POST | 20 | 20 | 100 | 50 | 60 | 100 | 90 | 0 |
| 41 | 4.00 | PES | 0 | 0 | 0 | 10 | 70 | 100 | 100 | 0 |
| | 4.00 | POST | 70 | 60 | 0 | 100 | 85 | 100 | 100 | 0 |
| 42 | 4.00 | PES | 0 | 0 | 0 | 20 | 0 | 100 | 85 | 0 |
| | 4.00 | POST | 90 | 50 | 40 | 100 | 100 | 100 | 100 | 0 |
| 43 | 4.00 | PES | 100 | 100 | 35 | 100 | 100 | 100 | 100 | 0 |
| | 4.00 | POST | 100 | 100 | 95 | 100 | 100 | 100 | 100 | 35 |
| 44 | 4.00 | PES | 95 | 95 | 0 | 40 | 50 | 90 | 85 | 0 |
| | 4.00 | POST | 100 | 100 | 100 | 100 | 100 | 100 | 100 | 20 |
| 47 | 4.00 | PES | 90 | 60 | 15 | 25 | 30 | 100 | 100 | 0 |
| | 4.00 | POST | 100 | 70 | 30 | 100 | N | 100 | 100 | 0 |
| 48 | 4.00 | PES | 0 | 0 | 0 | 0 | 0 | 0 | 0 | 0 |
| | 4.00 | POST | 60 | 20 | 10 | 100 | 80 | 100 | 15 | 0 |
| 49 | 4.00 | PES | 0 | 0 | 0 | 0 | 0 | 0 | 0 | 0 |
| | 4.00 | POST | 20 | 20 | 0 | 30 | 90 | 100 | 100 | 0 |
| 50 | 4.00 | PES | 0 | 0 | 0 | 0 | 0 | 0 | 50 | 0 |

TABLE I-continued

HERBICIDE TEST RESULTS

| Compound Number | Application Rate (lb/A) | Method | FT | WG | WO | AMG | VL | MD | CD | YNS |
|---|---|---|---|---|---|---|---|---|---|---|
| | 4.00 | POST | 0 | 0 | 0 | 60 | 100 | 100 | 80 | 0 |

TABLE 2

| Cmpd. No. | Application Rate (lb/A) | Method | Weed Species | | | | | | | | | | | | | | | Crop Species | | | | | | |
|---|---|---|---|---|---|---|---|---|---|---|---|---|---|---|---|---|---|---|---|---|---|---|---|---|
| | | | DB | FT | ARG | WG | SHC | WO | BSG | AMG | SESB | VL | SP | MD | YNS | CB | SOY | WH | ML | RC | SB | CN | COT |
| 5 | 0.25 | PES | N | N | N | N | N | N | N | 0 | 10 | 0 | 0 | 0 | 0 | 0 | 0 | 0 | 0 | 0 | 0 | 0 | 0 | 0 |
| | 0.50 | PES | N | N | N | N | N | N | N | 30 | 60 | 40 | 0 | 0 | 0 | 0 | 20 | 0 | 0 | 0 | 20 | 0 | 0 |
| | 1.00 | PES | N | N | N | N | N | N | N | 40 | 75 | 90 | 60 | 100 | 0 | 0 | 50 | 0 | 10 | 0 | 100 | 20 | 10 |
| | 2.00 | PES | 10 | 70 | 10 | 20 | 20 | 30 | 80 | 95 | 80 | 60 | 80 | 95 | 10 | 0 | 60 | 10 | 20 | 30 | 80 | 30 | 50 |
| | 0.25 | POST | 60 | 100 | 20 | 10 | 10 | 10 | 0 | 100 | 80 | 100 | 80 | 100 | 10 | N | 40 | 30 | 40 | 60 | 100 | 30 | 100 |
| | 0.50 | POST | 40 | 100 | 50 | 20 | 20 | 30 | 30 | 100 | 90 | 70 | 90 | 100 | 10 | N | 100 | 60 | 100 | 100 | 100 | 70 | 100 |
| | 1.00 | POST | 40 | 100 | 70 | 20 | 40 | 80 | 40 | 100 | 95 | 100 | 90 | 100 | 10 | 100 | 100 | 60 | 100 | 100 | 100 | 100 | 100 |
| | 2.00 | POST | 50 | 100 | 70 | 90 | 40 | 80 | 80 | 100 | 0 | 100 | 0 | 100 | 10 | 100 | 100 | 60 | 100 | 100 | 100 | 100 | 100 |
| 17 | 0.10 | PES | 0 | 0 | 0 | 0 | 0 | 0 | 0 | 0 | 0 | 0 | 0 | 0 | 0 | 0 | 0 | 0 | 0 | 0 | 0 | 0 | 0 |
| | 0.25 | PES | 10 | 20 | 10 | 10 | 10 | 60 | 0 | 20 | 50 | 30 | 30 | 90 | 50 | 20 | 30 | 0 | 10 | 10 | 50 | 30 | 20 |
| | 0.50 | PES | 40 | 100 | 40 | 20 | 20 | 50 | 50 | 60 | 70 | 100 | 60 | 100 | 10 | 0 | 60 | 20 | 30 | 20 | 100 | 50 | 60 |
| | 1.00 | PES | 60 | 100 | 70 | 80 | 30 | 60 | 70 | 100 | 90 | 100 | 60 | 100 | 30 | 20 | 60 | 30 | 50 | 40 | 100 | 60 | 100 |
| | 2.00 | PES | 20 | 20 | 40 | 10 | 10 | 10 | 10 | 70 | 80 | 100 | 90 | 100 | 10 | 0 | 80 | 20 | 10 | 80 | 100 | 60 | 100 |
| | 0.10 | POST | 60 | 20 | 80 | 30 | 20 | 20 | 20 | 100 | 100 | 100 | 80 | 100 | 30 | 0 | 80 | 30 | 30 | 100 | 100 | 60 | 100 |
| | 0.25 | POST | 70 | 100 | 70 | 30 | 50 | 30 | 80 | 100 | 100 | 100 | 90 | 100 | 30 | 100 | 100 | 30 | 100 | 100 | 100 | 60 | 100 |
| | 0.50 | POST | 70 | 100 | 70 | 30 | 50 | 100 | 80 | 100 | 100 | 100 | 100 | 100 | 30 | 100 | 100 | 40 | 100 | 100 | 100 | 100 | 100 |
| | 1.00 | POST | 100 | 100 | 60 | 100 | 80 | 30 | 50 | 100 | 70 | 100 | 100 | 100 | 0 | 100 | 35 | 0 | 45 | 40 | 95 | 20 | 0 |
| 25 | 2.00 | PES | 80 | 100 | 60 | 100 | 80 | 25 | 30 | 25 | 35 | 50 | 30 | 100 | 0 | N | 10 | 0 | 15 | 10 | 100 | 20 | 0 |
| | 1.00 | PES | 100 | 100 | 40 | 20 | 20 | 10 | 20 | 15 | 25 | 30 | 10 | 35 | 0 | Z | 0 | 0 | 30 | 0 | 30 | 10 | 0 |
| | 0.50 | PES | N | N | N | N | N | N | N | 5 | 10 | 30 | 10 | 20 | 0 | 0 | 0 | 0 | 0 | 0 | 0 | 0 | 0 |
| | 0.25 | N | N | N | N | N | N | N | N | 0 | 0 | 0 | 0 | 0 | 0 | 0 | 0 | 0 | 0 | 0 | 0 | 0 | 0 |
| | 2.00 | POST | 100 | 100 | 100 | 100 | 100 | 95 | 100 | 90 | 100 | 100 | 90 | 100 | 0 | 100 | 100 | 70 | 100 | 100 | 100 | 100 | 100 |
| | 1.00 | POST | 100 | 100 | 100 | 100 | 100 | 80 | 100 | 100 | 100 | 100 | 70 | 100 | 0 | 100 | 90 | 25 | 45 | 98 | 100 | 90 | 90 |
| | 0.50 | POST | 95 | 85 | 95 | 75 | 40 | 55 | 85 | 100 | 80 | 98 | 70 | 100 | 0 | 100 | 60 | 30 | 15 | 98 | 100 | 65 | 85 |
| | 0.25 | POST | 80 | 75 | 80 | 20 | 15 | 15 | 15 | 90 | 45 | 100 | 45 | 98 | 0 | 100 | 60 | 0 | 20 | 50 | 90 | 25 | 50 |
| 27 | 2.00 | PES | 60 | 100 | 50 | 10 | 40 | 0 | 0 | 80 | 100 | 80 | 80 | 100 | 0 | N | 80 | 30 | 45 | 40 | 100 | 10 | 100 |
| | 1.00 | PES | 50 | 100 | 50 | 35 | 15 | 0 | 0 | 90 | 100 | 100 | 20 | 100 | 0 | Z | 80 | 0 | 20 | 20 | 100 | 15 | 100 |
| | 0.50 | PES | N | N | N | N | N | N | N | 0 | 30 | 100 | 20 | 100 | 0 | 0 | 80 | 0 | 20 | 0 | 30 | 10 | 0 |
| | 0.25 | PES | N | N | N | N | N | N | N | 0 | 20 | 100 | 0 | 0 | 0 | 0 | 30 | 0 | 0 | 0 | 0 | 0 | 0 |
| | 2.00 | POST | 100 | 100 | 100 | 100 | 100 | 80 | 100 | 100 | 100 | 100 | 100 | 100 | 0 | 100 | 100 | 80 | 100 | 85 | 100 | 100 | 100 |
| | 1.00 | POST | 100 | 100 | 100 | 100 | 100 | 20 | 80 | 100 | 100 | 100 | 60 | 100 | 0 | 100 | 100 | 80 | 70 | 80 | 100 | 40 | 100 |
| 28 | 0.50 | POST | 85 | 85 | 95 | 75 | 65 | 55 | 85 | 100 | 100 | 100 | 60 | 100 | 0 | 100 | 80 | 40 | 50 | 80 | 100 | 40 | 85 |
| | 0.25 | POST | 60 | 75 | 80 | 20 | 80 | 15 | 15 | 90 | 80 | 100 | 45 | 85 | 0 | 100 | 80 | 40 | 20 | 25 | 100 | 35 | 50 |
| | 2.00 | PES | 50 | 100 | 50 | 10 | 40 | 0 | 15 | 100 | 100 | 100 | 80 | 100 | 0 | 15 | 98 | 20 | 45 | 45 | 100 | 50 | 90 |
| 30 | 1.00 | POST | 50 | 100 | 50 | 35 | 30 | 0 | 0 | 30 | 95 | 100 | 25 | 97 | 0 | 0 | 70 | 15 | 30 | 35 | 70 | 50 | 90 |
| 31 | 2.00 | POST | 20 | Z | Z | Z | 0 | Z | 0 | 10 | 35 | 40 | 20 | 100 | 0 | N | 30 | 30 | 20 | 20 | 30 | 0 | 15 |
| | 1.00 | POST | 100 | 100 | 100 | 100 | 100 | 80 | 100 | 100 | 100 | 100 | 100 | 100 | 60 | 0 | 100 | 100 | 100 | 100 | 100 | 100 | 95 |
| | 0.50 | PES | 90 | 100 | 100 | 100 | 100 | 80 | 98 | 100 | 100 | 98 | 85 | 60 | Z | 100 | 75 | 20 | 80 | 45 | 30 | 0 | 90 |
| | 0.25 | PES | 100 | 100 | 100 | 100 | 100 | 45 | 90 | 100 | 100 | 100 | 85 | 100 | 0 | 0 | 100 | 100 | 100 | 90 | 100 | 100 | 100 |
| | 2.00 | POST | 90 | 100 | 100 | 90 | 100 | 45 | 90 | 100 | 100 | 100 | 85 | 100 | 0 | Z | 100 | 20 | 100 | 90 | 100 | 90 | 100 |

TABLE 2-continued

| Cmpd. No. | Application Rate (lb/A) | Method | Weed Species | | | | | | | | | | | | | | Crop Species | | | | | | |
|---|---|---|---|---|---|---|---|---|---|---|---|---|---|---|---|---|---|---|---|---|---|---|---|
| | | | DB | FT | ARG | WG | SHC | WO | BSG | AMG | SESB | VL | SP | MD | YNS | CB | SOY | WH | ML | RC | SB | CN | COT |
| 32 | 2.00 | PES | 100 | 100 | 90 | 100 | 100 | 35 | 60 | 70 | 100 | 100 | 90 | 100 | 15 | 100 | 40 | 10 | 60 | 50 | 100 | 30 | 60 |
| | 1.00 | PES | 90 | 100 | 90 | 100 | 100 | 20 | 35 | 20 | 85 | 100 | 25 | 100 | 0 | 100 | 40 | 15 | 25 | 20 | 100 | 0 | 15 |
| | 0.50 | PES | 60 | 90 | 35 | 60 | 70 | 10 | 15 | 20 | 85 | 100 | 0 | 95 | 0 | N | 40 | 0 | 25 | 20 | 100 | 0 | 0 |
| | 0.25 | PES | 20 | 30 | 0 | 30 | 25 | 0 | 0 | 0 | 15 | 20 | 0 | 85 | 0 | 0 | 15 | 0 | 10 | 0 | 30 | 0 | 0 |
| | 2.00 | POST | 80 | 100 | 100 | 100 | 100 | 65 | 100 | 100 | 100 | 100 | 100 | 100 | 0 | 100 | 100 | 100 | 100 | 100 | 100 | 100 | 100 |
| | 1.00 | POST | 80 | 100 | 100 | 100 | 100 | 60 | 98 | 100 | 98 | 85 | 100 | 100 | 0 | N | 100 | 55 | 90 | 100 | 100 | 100 | 100 |
| | 0.50 | POST | 70 | 100 | 100 | 90 | 90 | 45 | 85 | 100 | 95 | 100 | 100 | 100 | 0 | 100 | 100 | 50 | 80 | 65 | 100 | 100 | 100 |
| | 0.25 | POST | 70 | 100 | 80 | 35 | 60 | 15 | 80 | 90 | 95 | 100 | 90 | 100 | 0 | 100 | 100 | 60 | 35 | 40 | 100 | 85 | 100 |
| 37 | 2.00 | PES | 80 | 100 | 50 | 95 | 95 | 30 | 90 | 95 | 95 | 100 | 90 | 100 | 0 | 100 | 85 | 40 | 45 | 30 | 100 | 20 | 40 |
| | 1.00 | PES | 90 | 100 | 40 | 95 | 100 | 15 | 85 | 65 | 90 | 100 | 25 | 100 | 0 | 100 | 40 | 15 | 35 | 15 | 100 | 15 | 15 |
| | 0.50 | PES | 25 | 100 | 20 | N | N | 20 | 25 | 15 | 65 | 65 | 20 | 85 | 30 | 100 | 35 | 0 | 10 | 0 | 30 | 0 | 15 |
| | 0.25 | PES | N | N | N | N | N | N | N | N | 15 | 100 | 98 | 100 | 0 | 0 | 30 | 0 | 0 | 0 | 70 | 0 | 0 |
| | 2.00 | POST | 85 | 100 | 100 | 100 | 100 | 85 | 100 | 100 | 100 | 100 | 65 | 100 | 0 | 100 | 100 | 30 | 100 | 100 | 100 | 100 | 100 |
| | 1.00 | POST | 85 | 100 | 100 | 100 | 100 | 70 | 100 | 100 | 100 | 100 | 70 | 100 | 0 | 100 | 100 | 30 | 90 | 100 | 100 | 70 | 100 |
| | 0.50 | POST | 90 | 100 | 100 | 100 | 100 | 60 | 100 | 100 | 100 | 100 | 60 | 60 | 0 | 100 | 100 | 30 | 70 | 100 | 100 | 45 | 100 |
| | 0.25 | POST | 65 | 100 | 100 | 60 | 90 | 50 | 90 | 100 | 100 | 90 | 35 | 100 | 0 | 100 | 100 | 25 | 0 | 0 | 100 | 0 | 10 |
| 47 | 2.00 | PES | 20 | 90 | 40 | 25 | 15 | 0 | 0 | 30 | 95 | 40 | 0 | 70 | 0 | 100 | 80 | 0 | 40 | 0 | 0 | 0 | 0 |
| | 1.00 | PES | 0 | 60 | 0 | 0 | 0 | 0 | 0 | 15 | 85 | 20 | 0 | 100 | 0 | N | 80 | 20 | 45 | 0 | 100 | 0 | 85 |
| | 2.00 | POST | 0 | 100 | 0 | 0 | 0 | 0 | 65 | 100 | 100 | 100 | 100 | 100 | 0 | 100 | 100 | 0 | 30 | 0 | 100 | 0 | 65 |
| | 1.00 | POST | 0 | 90 | 0 | 0 | 0 | 0 | 50 | 100 | 100 | 100 | 100 | 100 | 0 | 100 | 100 | 20 | 20 | 0 | 100 | 0 | 65 |
| | 0.50 | POST | 0 | 90 | 0 | 0 | 0 | 0 | 30 | 100 | 100 | 100 | 90 | 60 | 0 | 100 | 60 | 0 | 20 | 0 | 100 | 40 | 35 |
| | 0.25 | POST | 0 | 20 | 0 | 0 | 0 | 0 | 0 | 75 | 100 | 0 | 100 | 100 | 0 | N | 80 | 0 | 60 | 100 | 100 | 40 | 40 |
| 48 | 2.00 | POST | 15 | 0 | 0 | 0 | 0 | 0 | 0 | 100 | 100 | 0 | 0 | 60 | 0 | N | 80 | 60 | 20 | 30 | 100 | 40 | 40 |
| | 0.50 | POST | 10 | 0 | 0 | 0 | 0 | 0 | N | 80 | 100 | 0 | 100 | 100 | 0 | N | 80 | 30 | 60 | 25 | 100 | 10 | 15 |
| | 0.25 | POST | N | N | N | N | N | N | 0 | 75 | 30 | 80 | 20 | 45 | 0 | N | 75 | 0 | 25 | 0 | 100 | 20 | 40 |
| 49 | 2.00 | POST | 15 | 30 | 0 | 0 | 15 | 0 | 20 | 50 | 100 | 80 | 20 | 100 | 0 | N | 40 | 0 | 10 | 0 | 100 | 0 | 45 |
| | 1.00 | POST | 0 | 0 | 0 | 0 | 0 | 0 | 0 | 30 | 70 | 15 | 20 | 100 | 0 | N | 35 | 0 | 15 | 0 | 100 | 0 | 40 |
| | 0.50 | POST | 0 | 0 | 0 | 0 | 0 | 0 | 0 | 30 | 60 | 15 | 10 | 100 | 0 | N | 40 | 0 | 0 | 0 | 55 | 0 | 25 |

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, wateroil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic sufactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Post-emergent application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A pyrimidine having the formula

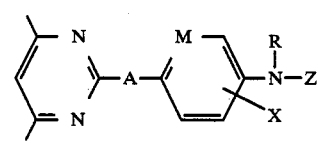

wherein
A is oxygen or sulfur;
M is N;
X is hydrogen, lower alkyl, halo, methoxy, alkoxy, $C_1$–$C_3$ alkylthio, cyano, carbomethoxy or trifluoromethyl;

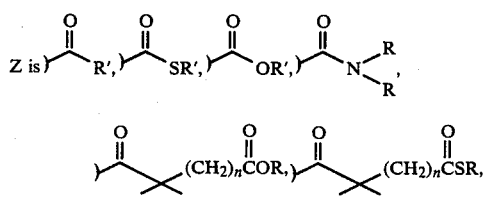

-continued

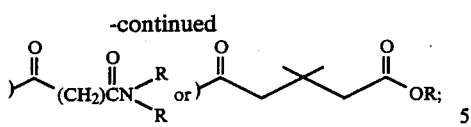

R' is C$_1$-C$_8$ straight, branched-chain or halo-alkyl, phenyl or halophenyl; and R is hydrogen, C$_1$-C$_8$ straight or branched chain alkyl, C$_5$ or C$_6$ cycloalkyl or phenyl or halophenyl; and n is zero to two.

2. A herbicidal composition which comprises a carrier and a herbicidally effective amount of a pyrimidine having the formula

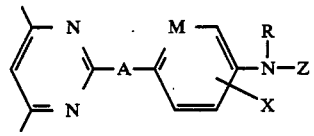

wherein
A is oxygen or sulfur;
M is N;
X is hydrogen, lower alkyl, halo, methoxy, alkoxy, C$_1$-C$_3$ alkylthio, cyano, carbomethoxy or trifluoromethyl;

Z is 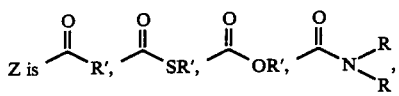

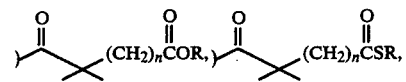

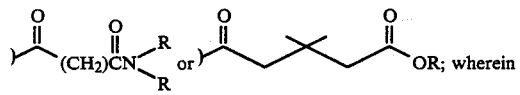 wherein

R' is C$_1$-C$_8$ straight, branched-chain or halo-alkyl, phenyl or halophenyl; and R is hydrogen, C$_1$-C$_8$ straight or branched chain alkyl, C$_5$ or C$_6$ cycloalkyl or phenyl or halophenyl; and n is zero to two.

3. A method for controlling undesirable weed pests which comprises applying to the locus where control is desired a herbicidally effective amount of a pyrimidine compound having the formula

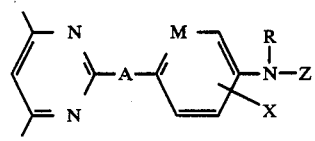

wherein
A is oxygen or sulfur;
M is N;
X is hydrogen, lower alkyl, halo, methoxy, alkoxy, C$_1$-C$_3$ alkylthio, cyano, carbomethoxy or trifluoromethyl;

Z is 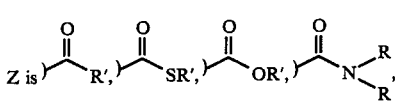

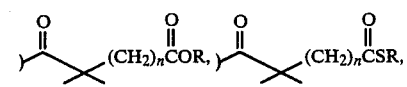

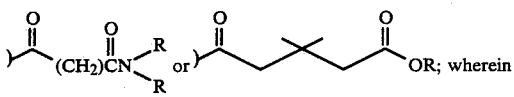 wherein

R' is C$_1$-C$_8$ straight, branched-chain or halo-alkyl, phenyl or halophenyl; and R is hydrogen, C$_1$-C$_8$ straight or branched chain alkyl, C$_5$ or C$_6$ cycloalkyl or phenyl or halophenyl; and n is zero to two.

* * * * *